US010128637B2

(12) United States Patent
Makino et al.

(10) Patent No.: US 10,128,637 B2
(45) Date of Patent: Nov. 13, 2018

(54) WAVELENGTH-TUNABLE VERTICAL CAVITY SURFACE EMITTING LASER FOR SWEPT SOURCE OPTICAL COHERENCE TOMOGRAPHY SYSTEM

(71) Applicant: Inphenix, Inc., Livermore, CA (US)

(72) Inventors: Toshihiko Makino, Livermore, CA (US); Tongning Li, Fremont, CA (US); David Eu, Fremont, CA (US)

(73) Assignee: InPhenix, Inc., Livermore, CA (US)

( * ) Notice: Subject to any disclaimer, the term of this patent is extended or adjusted under 35 U.S.C. 154(b) by 0 days.

(21) Appl. No.: 15/671,564

(22) Filed: Aug. 8, 2017

(65) Prior Publication Data

US 2018/0048121 A1 Feb. 15, 2018

Related U.S. Application Data

(63) Continuation of application No. 14/930,191, filed on Nov. 2, 2015, now Pat. No. 9,762,031, which is a (Continued)

(51) Int. Cl.
*H01S 5/183* (2006.01)
*H01S 5/34* (2006.01)
(Continued)

(52) U.S. Cl.
CPC ...... *H01S 5/18366* (2013.01); *G01B 9/02004* (2013.01); *G01N 21/4795* (2013.01);
(Continued)

(58) Field of Classification Search
CPC ............. H01S 5/18366; H01S 5/18311; H01S 5/3412; H01S 5/34313; H01S 5/18369
See application file for complete search history.

(56) References Cited

U.S. PATENT DOCUMENTS 6,339,603 B1 1/2002 Flanders
6,373,632 B1 4/2002 Flanders
(Continued)

FOREIGN PATENT DOCUMENTS

JP 2006-216722 A 8/2006
JP 2002-043696 A 2/2008
(Continued)

OTHER PUBLICATIONS

Chen et al., "Hybrid Quantum Well/Quantum Dot Structure for Broad Spectral Bandwidth Emitters",IEEE Journal of Selected Topics in Quantum Electronics, vol. 19, No. 4, 1900209 (2013).
(Continued)

*Primary Examiner* — Dung Nguyen
(74) *Attorney, Agent, or Firm* — McDermott Will & Emery LLP; Richard G. A. Bone (57) ABSTRACT

A wavelength-tunable vertical-cavity surface-emitting laser (VCSEL) with the use of microelectromechanical system (MEMS) technology is provided as a swept source for Optical Coherence Tomography (OCT). The wavelength-tunable VCSEL comprises a bottom mirror of the VCSEL, an active region, and a MEMS tunable upper mirror movable by electrostatic deflections. The bottom mirror comprising a GaAs based distributed Bragg reflector (DBR) stack, and the active region comprising multiple stacks of GaAs based quantum dot (QD) layers, are epitaxially grown on a GaAs substrate. The MEMS tunable upper mirror includes a membrane part supported by suspension beams, and an upper mirror comprising a dielectric DBR stack. The MEMS tunable quantum dots VCSEL can cover an operating wavelength range of more than 100 nm, preferably with a center wavelength between 250 and 1950 nm, and the sweeping rate can be from a few kHz to hundreds of kHz, and up to a few MHz.

9 Claims, 7 Drawing Sheets

Related U.S. Application Data continuation of application No. 14/321,792, filed on Jul. 1, 2014, now Pat. No. 9,203,215.

(60) Provisional application No. 61/842,389, filed on Jul. 3, 2013.

(51) Int. Cl.
  G01N 21/47 (2006.01)
  G01B 9/02 (2006.01)
  H01S 5/343 (2006.01)

(52) U.S. Cl.
  CPC ........ *H01S 5/18311* (2013.01); *H01S 5/3412* (2013.01); *H01S 5/18369* (2013.01); *H01S 5/34313* (2013.01)

(56) References Cited

U.S. PATENT DOCUMENTS

| | | | |
|---|---|---|---|
| 7,468,997 | B2 | 12/2008 | Jayaraman |
| 7,483,211 | B2 | 1/2009 | Nakamura |
| 7,701,588 | B2 | 4/2010 | Chang |
| 8,059,690 | B2 | 11/2011 | Chang-Hasnain |
| 9,203,215 | B2 | 12/2015 | Makino |
| 9,762,031 | B2 | 9/2017 | Makino |
| 2002/0114367 | A1 | 8/2002 | Stintz |
| 2002/0176474 | A1 | 11/2002 | Huang |
| 2003/0011864 | A1 | 1/2003 | Flanders |
| 2003/0016709 | A1 | 1/2003 | Flanders |
| 2007/0183643 | A1 | 8/2007 | Jayaraman |
| 2007/0189348 | A1 | 8/2007 | Kovsh |
| 2008/0165819 | A1 | 7/2008 | Lin |
| 2008/0212633 | A1 | 9/2008 | Shimizu |
| 2009/0303487 | A1 | 12/2009 | Bond |
| 2010/0316079 | A1 | 12/2010 | Chang-Hasnain |
| 2010/0316083 | A1* | 12/2010 | Chang-Hasnain ... G02B 5/0816 372/50.11 |
| 2014/0028997 | A1* | 1/2014 | Cable ................. G01B 9/02091 356/51 |
| 2014/0268169 | A1 | 9/2014 | Jayaraman |
| 2015/0153563 | A1 | 6/2015 | Kamal |

FOREIGN PATENT DOCUMENTS

| | | |
|---|---|---|
| JP | 2010-062426 A | 3/2010 |
| JP | 2010153739 A | 7/2010 |
| JP | 2011197883 A | 10/2011 |
| JP | 2012-191075 A | 10/2012 |
| WO | 2012/168545 A1 | 12/2012 |

OTHER PUBLICATIONS

Chinese Office Action from Chinese Patent Application No. 201480044416.1, dated Dec. 9, 2016.
Cole, "MEMS-tunable verticle-cavity SOAs", Thesis, UCSB (2005).
Cole et al., "Fabrication of suspended dielectric mirror structures via xenon difluoride etching of an amorphous germanium sacrificial layer", J. Vac. Sci. Technol. B, vol. 26, No. 2, pp. 593 (2008).
EPO Examination Report from EP Patent Application No. 14819362. 6, dated Jul. 28, 2016.
Hillmer et al., "Wide continuously tunable 1.55um vertical air-cavity wavelength selective elements for filters and VCSELs using micromachined actuation", Proc. of SPIE, vol. 5825 pp. 14-28 (2005).
International Search Report and Written Opinion in PCT/US2014/045170, dated Nov. 3, 2014.
International Search Report and Written Opinion in PCT/US2014/067477, dated Feb. 20, 2015.
Japanese Office Action from Japanese Patent Application No. 2015-653144, dated Jun. 28, 2016.
Jayaraman et al., "OCT imaging up to 760 kHz axial scan rate using single-mode 1310 nm MEMS-tunable VCSEL with>100 nm tuning range", Optical Society of America /CLEO: 2011—Laser Science to Photonic Applications, PDPB2 (2011).
Korean Office Action from Korean Patent Application No. 10-2016-7002932, dated Mar. 11, 2015.
Korean Examination Report from Korean patent Application No. 10-2016-7002932 dated Mar. 3, 2017.
Marschall et al., "Fourier domain mode-locked swept source at 1050 nm based on a tapered amplifier", Optics Express, vol. 18, No. 15, pp. 15820-15831 (2010).
Nishiyama et al., "Long-Wavelength Vertical-Cavity Surface-Emitting Lasers on InP With Lattice Matched AlGaInAs—InP DBR Grown by MOCVD", IEEE Journal of Selected Topics in Quantum Electronics, vol. 11, No. 5, pp. 990-998 (2005).
Peng et al., "Dynamic Characteristics and Linewidth Enhancement Factor of Quantum-Dot Vertical-Cavity Surface Emitting Lasers", IEEE Journal of Selected Topics in Quantum Electronics, vol. 15, No. 3, pp. 844-849 (2009).
Prott et al., "Modeling of ultrawidely tunable vertical cavity air-gap filters and VCSELs", IEEE Journal of Selected Topics in Quantum Electronrics, vol. 9, Issue 3, pp. 918-928 (2003).
Sugihwo et al., "Micromachined widely tunable vertical cavity laser diodes", J. of Microelectromechanical System, vol. 7, No. 1, pp. 48-55 (1998).
Takada et al., "10.3-Gb/s Operation over a Wide Temperature Range in 1.3-μm Quantum-dot DFB Lasers with High Model Gain", Optical Society of America / Optical Fiber Communication Conference\National Fiber Optic Engineers Conference, Technical Digest (2010).
U.S. Non-Final Office Action in U.S. Appl. No. 14/553,807, dated Jun. 18, 2015.
Yano et al., "Wavelength Modulation Over kHz of Micromechanically Tunable InP-Based VCSELs With Si-MEMS Technology", IEEE Journal of Selected Topics in Quantum Electronics, vol. 15, No. 3, pp. 528-534 (2009).
Zogal et al., "Singlemode 50nm tunable surface micro-machined MEMS-VCSEL operating at 1-95 m", Lasers and Electro-Optics (CLEO), 2012 Conference ON, IEEE, pp. 1-2 (2012).
Notice of Reasons of Refusal from Japanese Patent Application No. 2015-563144, 44 pages, dated May 22, 2018.

* cited by examiner

WAVELENGTH-TUNABLE VERTICAL CAVITY SURFACE EMITTING LASER FOR SWEPT SOURCE OPTICAL COHERENCE TOMOGRAPHY SYSTEM

CLAIM OF PRIORITY

This application is a continuation of application Ser. No. 14/930,191, filed Nov. 2, 2015, now U.S. Pat. No. 9,762,031, which application is a continuation of application Ser. No. 14/321,792, filed Jul. 1, 2014, now U.S. Pat. No. 9,203,215, which application claims the benefit of priority under 35 U.S.C. § 119(e) to U.S. provisional application Ser. No. 61/842,389, filed Jul. 3, 2013, all of which are incorporated herein by reference in their respective entireties.

TECHNICAL FIELD

The technology described herein generally relates to optical coherence tomography systems, and more particularly relates to such systems based on vertical cavity surface emitting laser devices.

BACKGROUND

Optical Coherence Tomography (OCT) is a technique for high-resolution depth profiling of a sample (biological samples such as tissues, organs, living bodies, or industrial samples such as polymers, thin-films). There are two types of OCT, namely, a time-domain OCT (TD-OCT), and a frequency-domain OCT (FD-OCT). In TD-OCT, the broadband light source is typically a superluminescent diode, which simultaneously emits multiple wavelengths; by scanning the position of a reference mirror, the frequencies of interference components in the reflecting light from the sample are analyzed. In FD-OCT, a swept source type OCT (SS-OCT), which employs a wavelength tunable laser as the broadband source, has become more widely used. In SS-OCT, only one wavelength is present at any one time, and sweeping of the laser wavelength replaces the mechanical scanning of the reference mirror. The signal to noise ratio of SS-OCT is fundamentally better than that of TD-OCT.

For a tunable laser for use in SS-OCT, requirements include: single-mode operation, a wide tuning range, high scan rate of wavelength, and wavelength tuning that is a simple monotonic function of a tuning control signal.

A tunable VCSEL with a MEMS that utilizes two distributed Bragg reflectors (DBR) has been reported. Such a device employs a bottom mirror consisting of a lower DBR composed of multiple alternating layers of AlGaInAs and InP, and an active layer composed of InP-based multiple quantum wells (MQWs) and barriers, which are all grown on a InP substrate, and a MEMS tunable upper DBR. The device has a tuning range of 55 nm at a center wavelength around 1550 nm. This tuning range is not sufficient for a number of applications.

Figure 1:
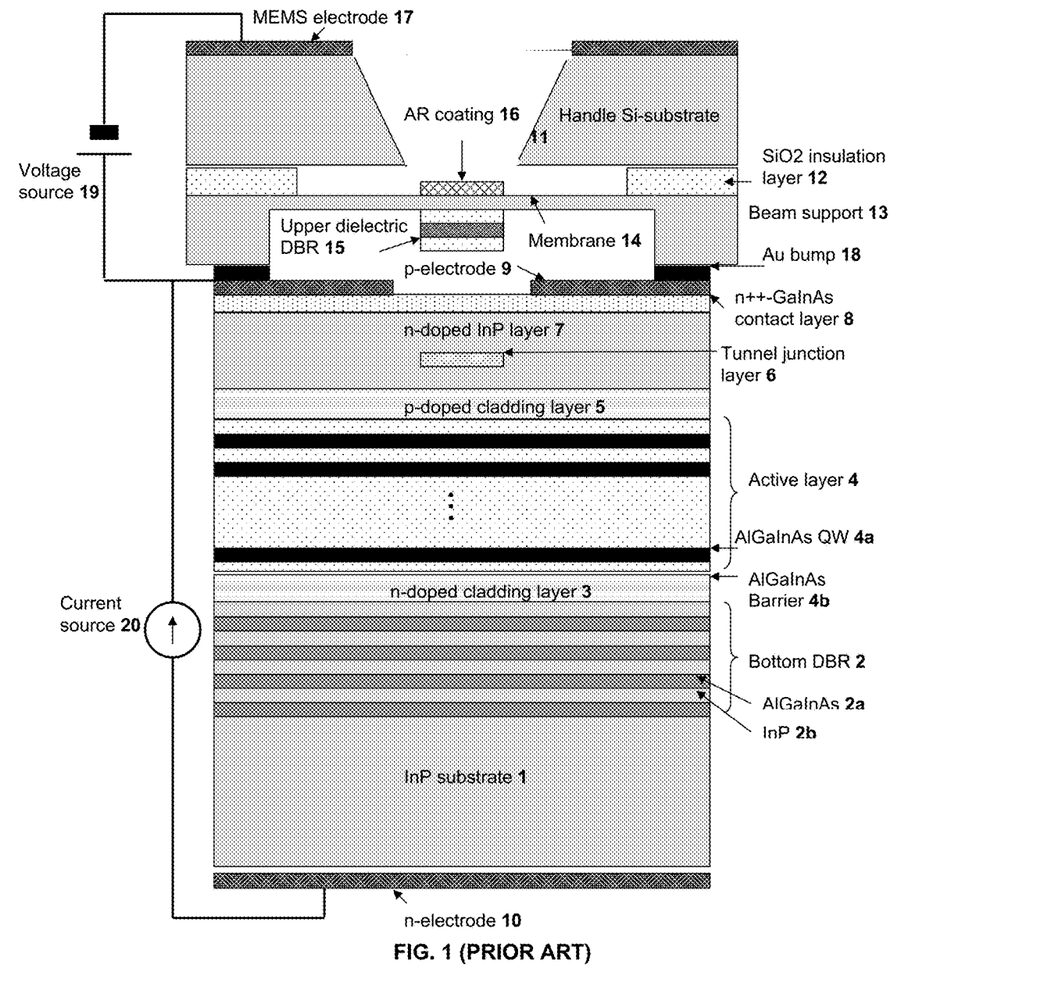
FIG. 1 is a schematic of a prior art MEMS tunable VCSEL.

FIG. 1 illustrates such a tunable VCSEL with MEMS, as known in the art. On a InP substrate 1, a n-doped distributed Bragg reflector (DBR) 2 consisting of over 40 pairs (not all shown) of alternating layers of AlGaInAs 2a (lattice-matched to InP) and InP 2b are epitaxially grown, followed by a n-type AlGaInAs cladding layer 3. On the top of the cladding layer 3, an active layer 4 consisting of multiple (six) AlGaInAs quantum wells ("QWs") 4a and multiple (seven) AlGaInAs barriers 4b are grown, followed by a p-type AlGaInAs cladding layer 5. Above the p-type cladding layer 5, a $p^{++}$-doped-AlGaInAs/$n^{++}$-doped-AlGaInAs tunnel junction layer 6 is grown to allow the replacement of a p-type InP layer with a n-doped InP layer since the tunnel junction can convert electrons to holes, which is followed by a n-doped InP layer 7 and a $n^{++}$-doped GaInAs contact layer 8. VCSEL p-electrode 9 is formed on the top of the contact layer 8 and n-electrode 10 is formed on the substrate 1, to complete the "half VCSEL" structure. On the top of the half VCSEL structure, an independently manufactured upper mirror part is bonded to the half VCSEL structure. The independently manufactured upper mirror part is formed on a "handle" Si-substrate 11 that bonds the two layers together. A $SiO_2$ layer 12 is formed as an insulation layer, followed by a beam support layer of Si 13. A thin membrane 14 is formed by etching the $SiO_2$ layer 12 as a sacrificial layer. An upper dielectric DBR 15 is deposited on one side of the membrane 14, and an antireflection (AR) coating 16 is deposited on the opposite side. A MEMS electrode 17 and Au-bumps 18 are formed to supply the MEMS voltage, which can change the air gap between the contact layer 8 and the upper DBR 15. An electric voltage source 19 is connected with the MEMS electrode 17 and with the p-electrode 9. Therefore, the membrane 14 can be moved by the electrostatic force induced by the electric voltage source 19, thereby changing the cavity length formed between the upper and bottom DBR mirrors, which in turn changes the lasing wavelength. An electric current source 20 is connected for current injection to the half VCSEL part.

Details of a device such as in FIG. 1 are described in T. Yano, H. Saitou, N. Kanbara, R. Noda, S. Tezuka, N. Fujimura, M. Ooyama, T. Watanabe, T. Hirata, and Nishiyama, "Wavelength modulation over 500 kHz of micromechanically tunable InP-based VCSELs with Si-MEMS technology", *IEEE J.*, Selected Topics in Quantum Electronics, vol. 15, pp. 528-534, May/June 2009, incorporated herein by reference. VCSEL's with fixed lasing wavelengths of 1310 nm and 1550 nm, utilized in the prior art, are described in N. Nishiyama, C. Caneau, B. Hall, G. Guryanov, M. H. Hu, X. S. Liu, M. -J. Li, R. Bhat, and C. E. Zah, "Long-wavelength vertical-cavity surface-emitting lasers on InP with lattice matched AlGaInAs-InP DBR grown by MOCVD", *IEEE J.*, Selected Topics in Quantum Electronics, vol. 11, pp. 990-998, September/October 2005, incorporated herein by reference.

In the prior art configuration of FIG. 1, a tuning range of 55 nm at a center wavelength around 1550 nm has been shown. The maximum tuning range is limited by the reflectivity bandwidth of the bottom DBR, which is determined by the ratio of the refractive indices of high-index and low-index materials. The reflectivity bandwidths of a DBR composed of alternating layers of AlGaInAs (high-index material) and InP (low-index material) are approximately 50 nm and 70 nm for center wavelengths of 1310 nm and 1550 nm, respectively. However, SS-OCT requires over 100 nm tuning range. Therefore, the VCSEL employing a DBR composed of AlGaInAs and InP and an active layer comprising quantum wells is not suitable for OCT applications.

To overcome this tuning range limitation, a tunable VCSEL with MEMS has been suggested, that employs a bottom mirror consisting of a DBR composed of alternating layers of AlGaAs (high-index material) and $Al_xO_y$ (low-index material) that has a reflectivity bandwidth over 200 nm centered near 1300 nm. This type of tunable VCSEL has achieved a tuning range over 100 nm by optical pumping. The details are described in V. Jayaraman, J. Jiang, H. Li, P. J. S. Heim, G. D. Cole, B. Potsaid, J. G. Fujimoto, and A. Cable, "OCT imaging up to 760 kHz axial scan rate using single-mode 1310 nm MEMS-tunable VCSEL with >100 nm tuning range", CLEO: 2011—Laser Science to Photonic Applications, PDPB2, 2011, incorporated herein by reference. In this approach, the active region comprises InP based multiple quantum wells (MQWs) epitaxially grown on an InP substrate. The bottom DBR is epitaxially grown on a GaAs substrate. Therefore, the materials in the active region and the DBR part cannot be grown on a single type substrate. The two wafers must be bonded together, and then the InP substrate needs to be removed in order to form the half VCSEL part. Bonding the GaAs and InP wafers and the removing the InP wafer requires a very complicated process and introduces potential reliability issues.

Quantum dot (QD) lasers have been investigated with the aim of replacing conventional quantum-well lasers. QD lasers have unique characteristics such as ultra-low threshold currents and low temperature sensitivity due to the three-dimensional quantum size effect. Quantum dot technology has progressed significantly by the self-assembling growth technique of InAs QD's on large GaAs substrates. Application of QD's to conventional edge emitting lasers (as opposed to VCSEL systems) has been accomplished by replacing quantum wells of the active layer by QD's. The high performance of 1.3 μm QD Distributed Feedback (DFB) lasers has been reported recently. These lasers are fabricated by molecular beam epitaxy (MBE) of 8 stacks of a high density QD layer with p-doped GaAs layers on a p-type GaAs substrate. The gain spectrum has been measured: a maximum net modal gain as high as 42 cm$^{-1}$ at around 1280 nm is obtained, and the 3 dB gain bandwidth is approximately 65 nm. The details are described in K. Takada, Y. Tanaka, T. Matsumoto, M. Ekawa, H. Z. Song, Y. Nakata, M. Yamaguchi, K. Nishi, T. Yamamoto, M. Sugawara, and Y. Arakawa, "10.3 Gb/s operation over a wide temperature range in 1.3 μm quantum-dot DFB lasers with high modal gain", Optical Fiber Communication Conference\National Fiber Optic Engineers Conference, (2010), Technical Digest, incorporated herein by reference.

A 1.3 μm VCSEL comprising QD's for fixed wavelength applications has also been reported recently: On a GaAs substrate, a bottom DBR composed of 33.5 pairs of n$^+$-doped AlGaAs layer and n$^+$-doped GaAs layer, an undoped active region composed of InAs/InGaAs QD's, a p-doped AlGaAs oxidation layer, and a upper DBR composed of 22 pairs of p$^+$-doped AlGaAs layers and p$^+$-doped GaAs layers, are grown by MBE. The lasing wavelength is around 1279 nm at room temperature. A small linewidth enhancement factor of 0.48 has also been reported, which can provide a narrow linewidth that is critical for OCT applications. The details are described in P. -C. Peng, G. Lin, H. -C. Kuo, C. E. Yeh, J. -N. Liu, C. -T. Lin, J. Chen, S. Chi, J. Y. Chi, S. -C. Wang, "Dynamic characteristics and linewidth enhancement factor of quantum-dot vertical-cavity surface-emitting lasers", IEEE J. Selected Topics in Quantum Electronics, vol. 15, pp. 844-849, May/June 2009, incorporated herein by reference.

The discussion of the background herein is included to explain the context of the technology. This is not to be taken as an admission that any of the material referred to was published, known, or part of the common general knowledge as at the priority date of any of the claims found appended hereto.

Throughout the description and claims of the specification the word "comprise" and variations thereof, such as "comprising" and "comprises", is not intended to exclude other additives, components, integers or steps.

SUMMARY

The present invention includes a microelectromechanical system (MEMS) tunable vertical cavity surface-emitting laser (VCSEL) comprising one or more layers of quantum dots.

The present invention includes a novel MEMS tunable quantum dot-based VCSEL swept source design having a narrow dynamic line width with a wide tuning range, necessary for deeper tomographic imaging with higher axial resolution. The present invention provides a MEMS tunable quantum dot VCSEL that solves at least two problems in the prior art: (1) insufficient DBR reflectivity bandwidth of InP based DBR, and (2) complicated wafer bonding required for two different types of wafers, (as in, for example, an InP based active region wafer and a GaAs based DBR wafer). In the present invention, a GaAs based DBR with high reflection bandwidth and an active region of optical gain peak wavelength (including an exemplary embodiment centered around 1300 nm) can be epitaxially grown on a GaAs substrate, continuously without wafer bonding.

The MEMS tunable VCSEL includes an upper vertically movable mirror part and a bottom half VCSEL part. The upper mirror part includes: a membrane part supported by suspension beams, and an upper DBR provided on the membrane for reflecting light. The bottom half VCSEL part includes a bottom GaAs based DBR, an active region consisting of quantum dots which are epitaxially grown on top of the bottom DBR, and formed in a position facing the top DBR layer of the top mirror part via a gap. The cavity length of the cavity formed between the upper DBR and the bottom DBR can be changed by changing the gap distance through application of an electrostatic force to the membrane. Therefore, the lasing wavelength can be continuously changed with high speed. Since the VCSEL oscillates in a single mode, sample detection sensitivity is high in that the internal detectable depth is as deep as 50 mm in the SS-OCT system.

BRIEF DESCRIPTION OF THE DRAWINGS

FIG. 4b is a cross-section view along the A-A line of the upper mirror part in the embodiment of FIG. 4a;

Like reference symbols in the various drawings indicate like elements.

DETAILED DESCRIPTION

Figure 2:
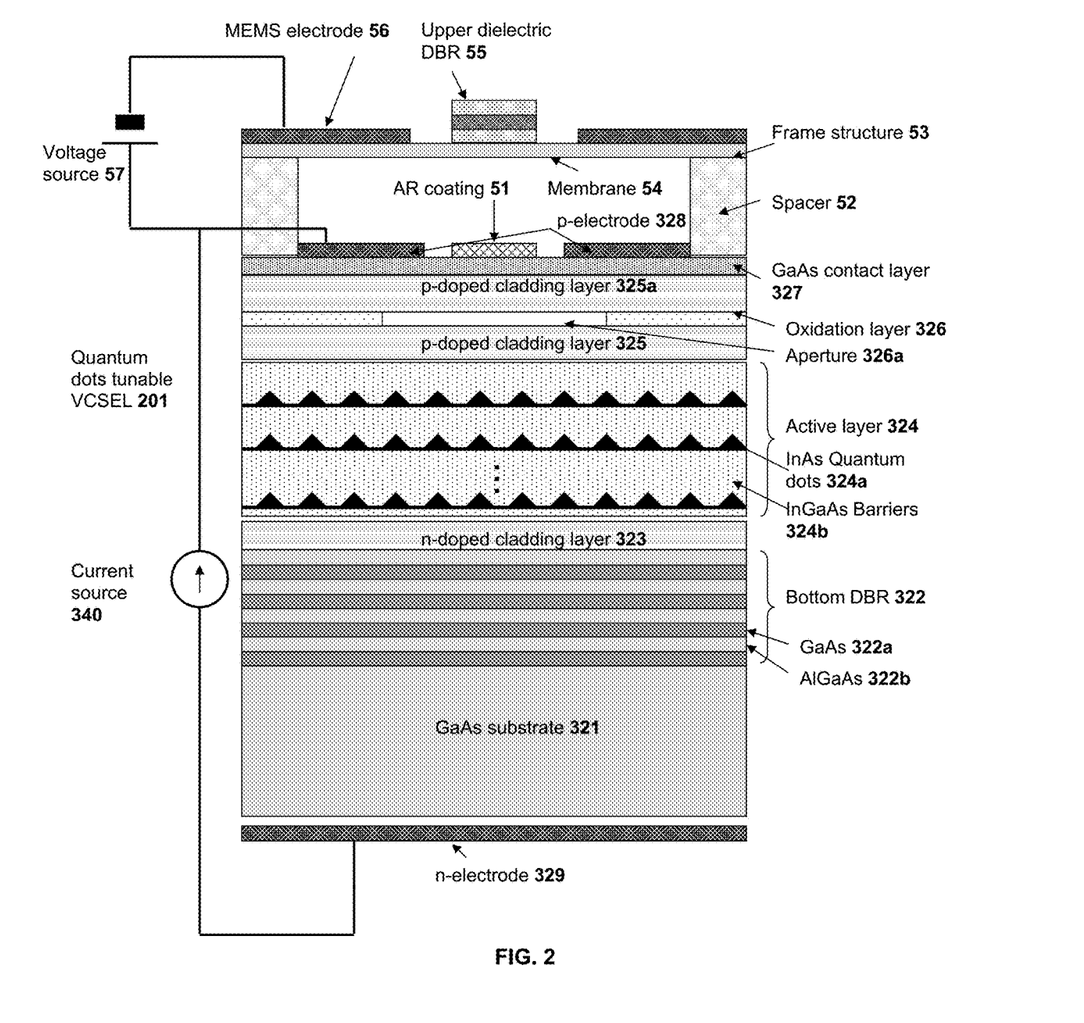
FIG. 2 is a schematic representation of a MEMS tunable quantum dot VCSEL according to one exemplary embodiment of the present invention.
Figure 3:
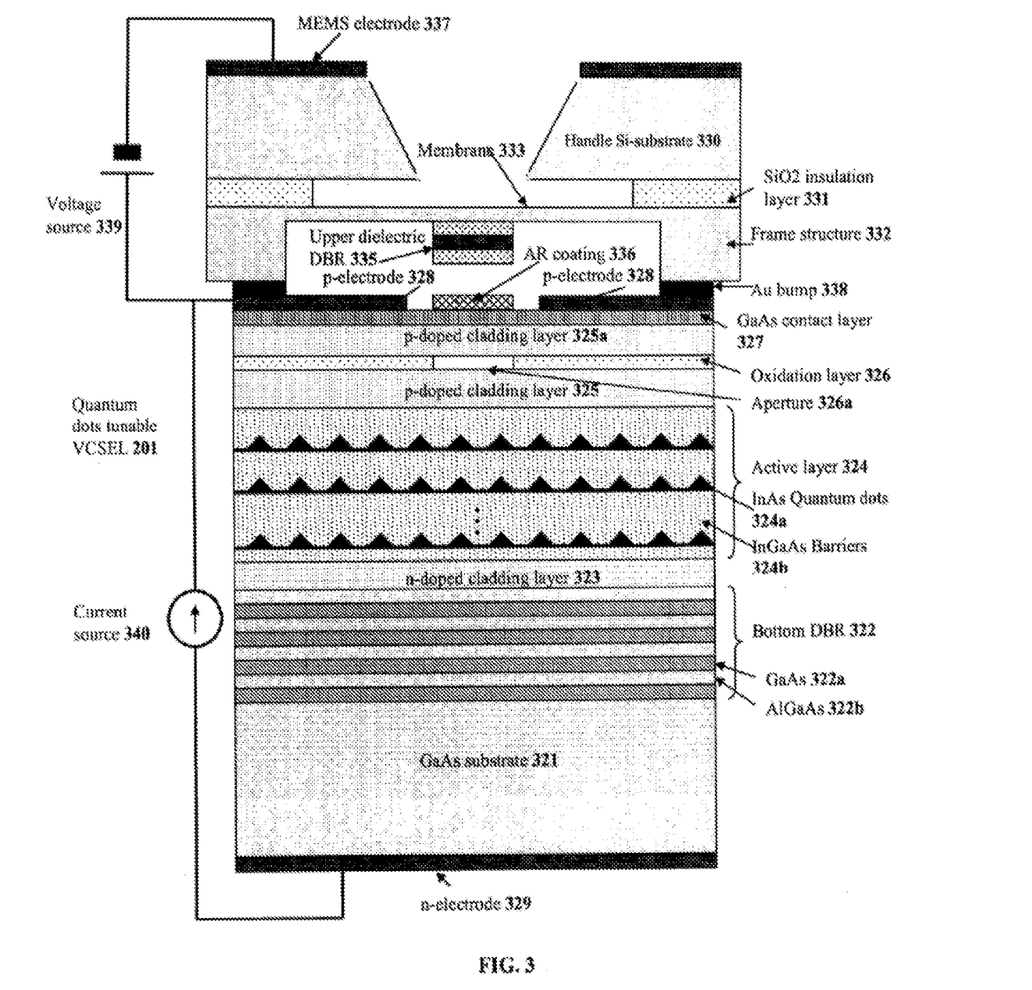
FIG. 3 is a schematic representation of a MEMS tunable quantum dot VCSEL according to a second exemplary embodiment of the present invention.

The technology of the present invention is exemplified by the two embodiments shown in FIGS. 2 and 3, respectively.

Each embodiment in FIGS. 2 and 3 comprises a pair of DBR's, one in the lower VCSEL half, and one in the upper MEMS portion. The two embodiments differ in the configuration of the upper (MEMS) half of each device. Both upper portions have the same overall function, and contain a membrane, an air gap and an upper (dielectric) DBR. The laser frequency is generated from a combination of the two DBR's and the air gap in between them.

FIG. 2 shows a schematic of an exemplary embodiment of the MEMS tunable quantum dot VCSEL of the present invention. On GaAs substrate 321, a n-doped DBR 322 consisting of 30 to 40 pairs of alternating layers of GaAs 322a, and AlGaAs 322b lattice matched to GaAs, is epitaxially grown, followed by a n-doped GaAs cladding layer 323. Then, an active layer 324 consisting of multi-layer stacks of InAs quantum dots (QD's) 324a (for example, lateral size of about 20 nm and a height of about 5 nm) alternating with InGaAs barrier layers 324b, are grown, followed by a p-doped AlGaAs cladding layer 325. Other size quantum dots are acceptable, for example having an average diameter of 5-8 nm, though may be 10 nm in size or up to 30 nm. The dot density in each layer 324a is typically in the range $10^{10}$-$10^{11}$ dots/cm$^2$. This is expressed as a "surface area density", since each layer typically supports only a single layer of dots. There are typically 8-20 layers per stack in the active layer, where each layer is up to about 40 nm thick, preferably 10-30 nm thick. Other numbers of layers are also consistent with the devices herein. The quantum dots are preferably made from InAs, though may be made from InGaAs, consistent with the operation of the overall technology. Quantum dots thereby provide different properties and functions in the active layer, when compared to the quantum wells previously used in the art. The quantum dots in the active layers may consist of dots of different sizes, as well as different compositions. In some embodiments, the quantum dots have a second quantized energy state (that is beneficial because it broadens the available spectrum to shorter wavelengths).

Above the cladding layer 325, an AlGaAs oxidation layer 326 and a further p-doped AlGaAs cladding layer 325a are grown. The oxidation layer 326 is partly oxidized except in a center region, referred to as aperture 326a having a diameter of 3 to 8 μm, to which an injection current (from 325a to the center region of 325) is confined (326 inhibits the current flow due to oxidation). On the top of cladding layer 325a, a p-doped GaAs contact layer 327 is grown. VCSEL p-electrode 328 and n-electrode 329 (typically made of Ti, Pt, or Au and Cr, Ni, or Au respectively) are formed on the top of the contact layer 327 and the bottom of substrate 321, respectively, to complete a half VCSEL structure.

After depositing an anti-reflection (AR) coating 51 on the GaAs contact layer 327, the top half MEMS is formed by depositing a spacer layer 52, composed of, for example, amorphous Ge, which is followed by a frame structure 53, composed of, for example, silicon nitride (SiN$_x$). A membrane 54 is formed by etching the spacer layer 52. In FIG. 2, items 53 and 54 correspond to frame structure 332, and to membrane 333, respectively, in FIG. 4(a). An upper dielectric DBR 55, comprised of alternating layers of, for example, TiO$_2$ and SiO$_2$, or Al$_2$O$_3$ and a-Si (amorphous silicon), is deposited on one side of the membrane 54. A MEMS electrode 56 is formed on frame structure 53. An electric voltage source 57 is connected between the electrode 56 and the p-metal (typically Ti, Pt or Au) electrode 328, to supply a MEMS voltage. Therefore, the membrane 54 can be deflected vertically by the electrostatic force induced by the voltage source 57. This deflection can change the cavity length formed between the upper DBR 55 and the bottom DBR 322, which changes the lasing wavelength. It is to be understood that where particular materials are specified for various layers and portions of the structure in FIG. 2, other materials having equivalent functions and properties could be used in their place, according to considerations understood to those of skill in the art.

FIG. 3 shows a schematic of another exemplary embodiment of the MEMS tunable quantum dot VCSEL of the present invention. On GaAs substrate 321, a n-doped DBR 322 consisting of 30 to 40 pairs of alternating layers of GaAs 322a, and AlGaAs 322b lattice matched to GaAs, is epitaxially grown, followed by a n-doped GaAs cladding layer 323. Then, an active layer 324 consisting of multi-layer stacks of InAs quantum dots (QD's) 324a (for example, lateral size of about 20 nm and a height of about 5 nm) alternating with InGaAs barrier layers 324b are grown, followed by a p-doped AlGaAs cladding layer 325. Above the cladding layer 325, an AlGaAs oxidation layer 326 and a p-doped AlGaAs layer 325a are grown. The oxidation layer 326 is partly oxidized except in a center region, referred to as aperture 326a, having a diameter of 3~8 μm, to which an injection current (from 325a to the center region of 325) is confined. The oxidation layer 326 inhibits the current flow because the oxide is a poor conductor. On the top of the cladding layer 325a, a p-doped GaAs contact layer 327 is grown, and thereafter an anti-reflection (AR) coating 336 is deposited on the GaAs contact layer 327.

VCSEL p-electrode 328 and n-electrode 329 are formed on the top of the contact layer 327 and the bottom of substrate 321, respectively, to complete a half VCSEL structure. To the extent thus far described, the structure of FIG. 3 is the same as that in FIG. 2. In the embodiment of FIG. 3, on the top of the half VCSEL structure, an independently manufactured top mirror part is bonded with a method such as thermo-compression The embodiment of FIG. 3 is therefore made differently from that of FIG. 2: in FIG. 2, the device can be manufactured from the bottom all the way up to the topmost layer (i.e., based on a single substrate). The device of FIG. 3, by contrast, is made in two pieces. The bottom half of the VCSEL is deposited on the substrate, layer by layer, whereas the upper MEMS portion is made separately, and then attached to the bottom half.

Figure 4A:
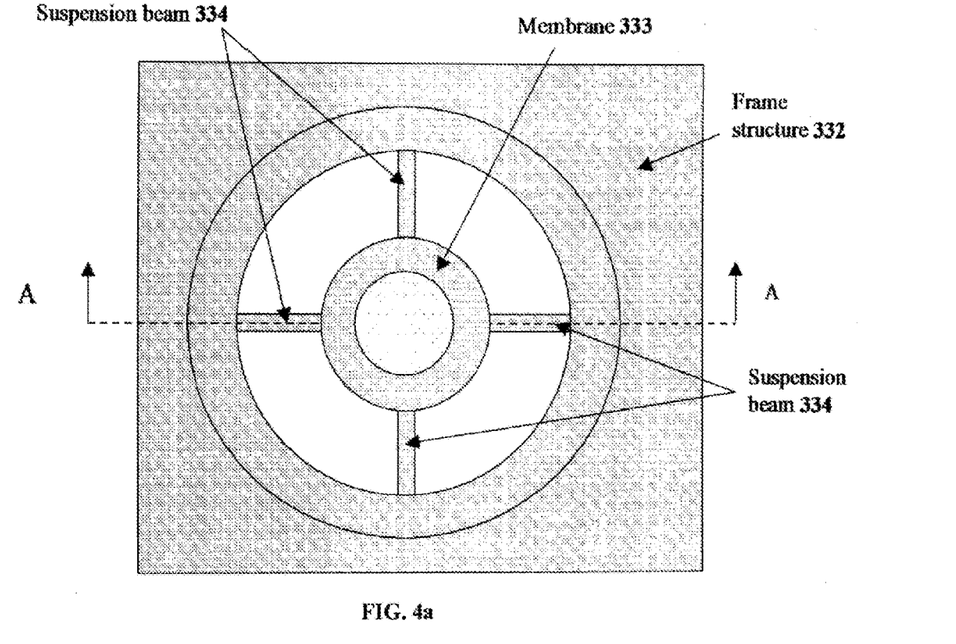
FIG. 4a is a top view of an upper mirror part of a MEMS tunable VCSEL according to an embodiment of the present invention.
Figure 4B:
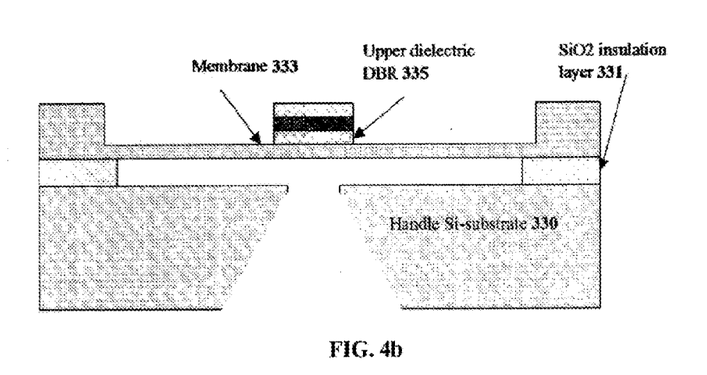

FIG. 4a is a top view of a vertically movable upper mirror part of a VCSEL according to the embodiment of FIG. 3. FIG. 4b is a cross-sectional view along the A-A line of FIG. 4a. The portion shown in FIG. 4b corresponds to the upper part of the device of FIG. 3; it is shown inverted relative to FIG. 3 in order to illustrate the manner in which it is made (by deposition of layers on to a substrate 330 that then becomes the top of the device). The movable upper mirror part is formed on a handle Si-substrate 330, as follows. The MEMS part is made independently from the half VCSEL part, and bonded through the Au bumps 338 to the half VCSEL part. The Si-substrate 330 thereby functions like a kind of handle for bonding the two parts to one another. A SiO$_2$ layer 331 is formed as an insulation layer, followed by a frame structure 332. A thin circular membrane 333 is formed, supported by four suspension beams 334 (FIG. 4a), which are formed by etching the SiO$_2$ layer 331 as a sacrificial layer. An upper dielectric DBR 335, comprised of alternating layers of, for example, TiO$_2$ and SiO$_2$, or Al$_2$O$_3$ and a-Si, is deposited on one side of the membrane 333. As shown in FIG. 3, a MEMS electrode 337 is formed on the substrate 330, and gold (Au) bumps 338 are formed on membrane 333. Typically, within the upper MEMS part, layers 331, 332/333 and 338 are formed in sequence on the Si substrate 330.

The upper mirror part (shown in FIG. 4a) is bonded to the p-electrode 328 via Au bumps 338 (with a method such as thermo-compression). An electric voltage source 339 is connected between the MEMS electrode 337 and the p-metal (typically Ti, Pt or Au) electrode 328, to supply a MEMS voltage. Therefore, the membrane 333 can be deflected vertically by the electrostatic force induced by the voltage source 339. This deflection can change the cavity length formed between the upper DBR 335 and the bottom DBR 322, which thereby changes the lasing wavelength. An electric current source 340 is connected to provide current injection to the active region 324. It is to be understood that where particular materials are specified for various layers and portions of the structures in FIGS. 3, 4a and 4b, other materials having equivalent functions and properties could be used in their place, according to considerations understood to those of skill in the art.

Figure 5:
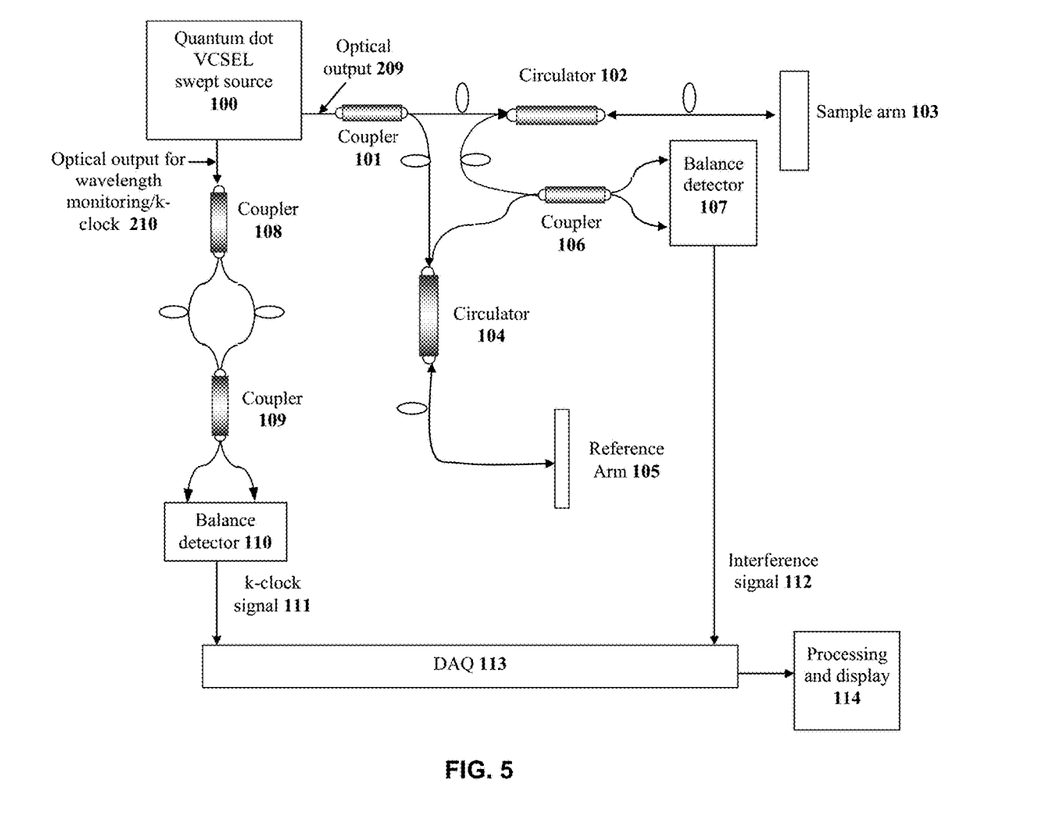
FIG. 5 is a schematic representation of a swept source optical coherence tomography system (SS-OCT) based on a MEMS tunable quantum dot VCSEL of the present invention.

FIG. 5 shows a schematic of a swept source optical coherence tomography system (SS-OCT) based on a MEMS tunable quantum dots VCSEL swept source utilizing a MEMS tunable quantum dot VCSEL such as shown in FIGS. 2, and 3, 4a and 4b. In this embodiment, the MEMS tunable quantum dots VCSEL swept source 100 has an optical output 209 that is then divided into two parts via fiber optic coupler 101. One division of wave output is directed through a circulator 102 to a sample arm 103. Another division from the fiber optic coupler 101 is directed through circulator 104 to reference arm 105. Reflected wave from sample arm 103 and reference arm 105 are recombined through fiber optic coupler 106, and the recombined wave is detected by balance detector 107 to give interference signal 112. Wavelength monitoring/k-clock output 210 is divided in two parts through fiber optic coupler 108 and recombined through fiber optic coupler 109 that is detected by balance detector 110 to give k-clock signal 111. A data acquisition card (DAQ) 113 is used to collect interference signal 112 and k-clock signal 111, and a reconstructed depth profile is displayed through processing and display module 114. Components such as couplers, balance detectors, and circulators, are typically off-the-shelf components that can be used with the technology described herein with little modification.

Figure 6A:
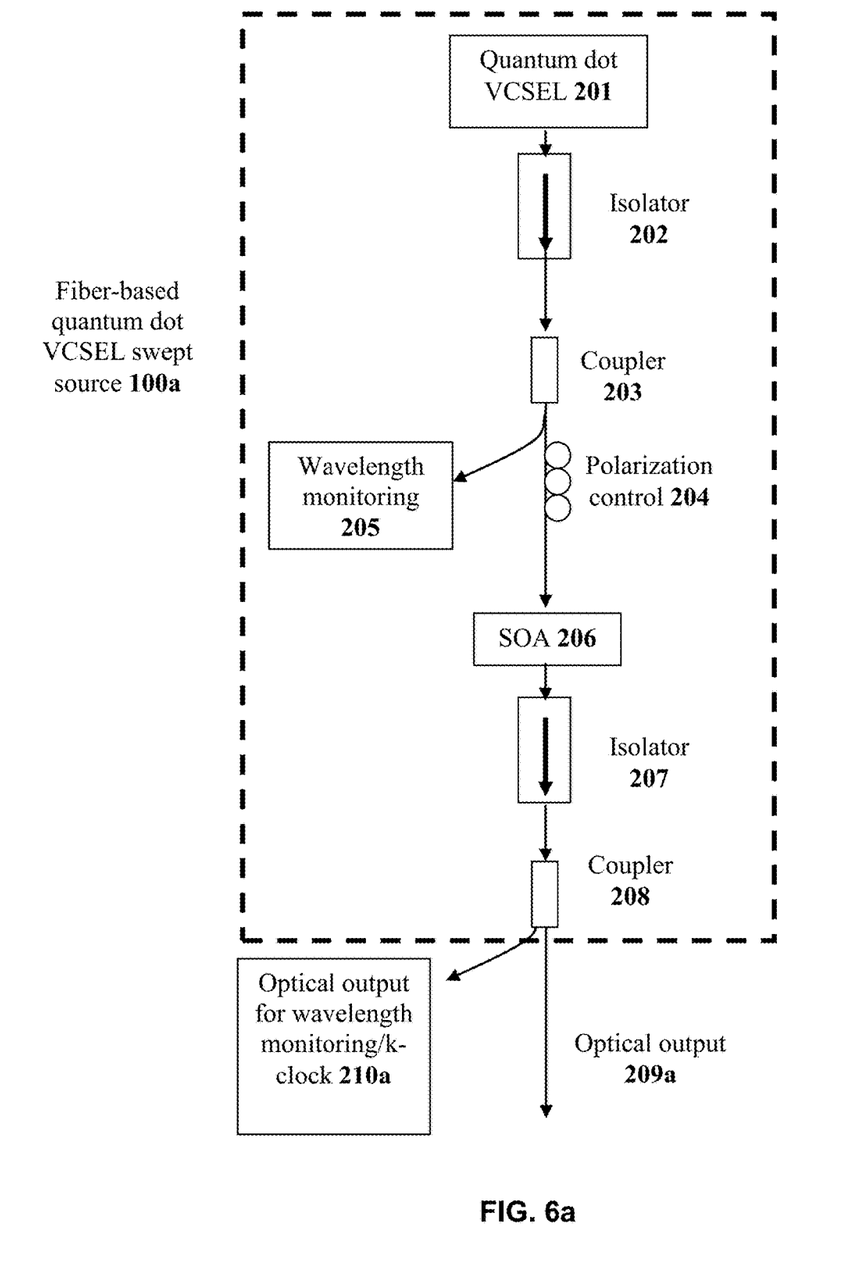
FIG. 6a is a schematic of a fiber based MEMS tunable quantum dot VCSEL swept source.

Regarding the MEMS tunable quantum dots VCSEL swept source 100 shown in FIG. 5, there are two exemplary embodiments (fiber based and free space based). FIG. 6a shows a schematic of an exemplary fiber based MEMS tunable quantum dots VCSEL swept source (100a). This embodiment comprises quantum dot tunable VCSEL 201 (such as one shown in FIG. 2, or in FIGS. 3, 4a and 4b), isolator 202, fiber optic coupler 203, semiconductor optical amplifier (SOA) 206, isolator 207 and fiber optic coupler 208. Optical output 209a and another output for wavelength monitoring/k-clock 210a comes from fiber optic coupler 208. An additional output from coupler 203 can be added for post amplification wavelength monitoring 205, and a polarization control 204 can be used to maximize power after amplification through SOA 206. Items 202, 203, 206, 207, 208, 209a, and 210 are off-the-shelf items that can be used without much modification.

Figure 6B:
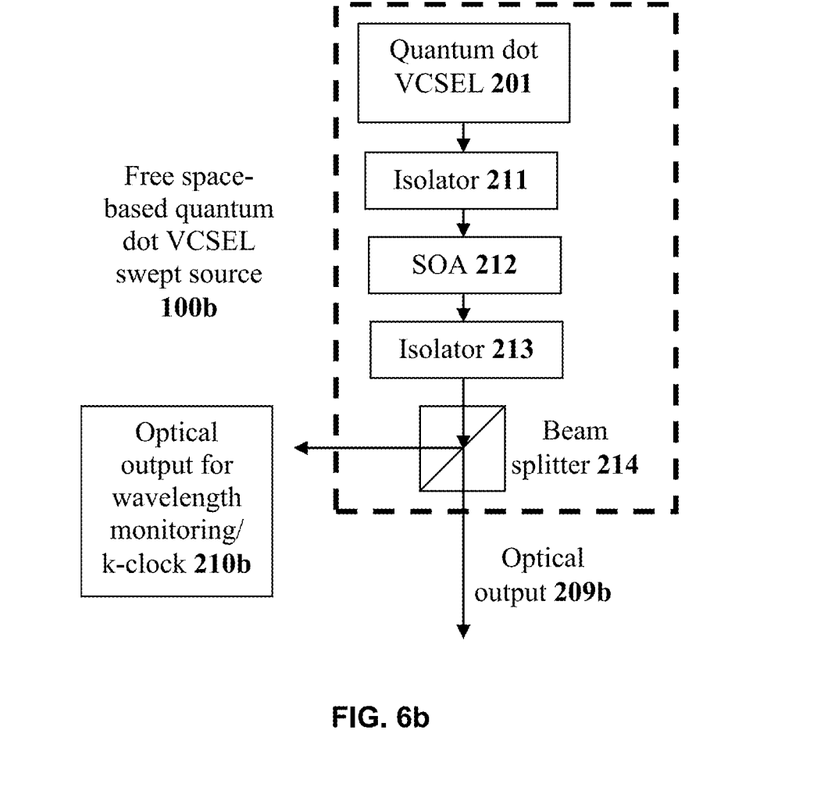
FIG. 6b is a schematic of a free space based MEMS tunable quantum dot VCSEL swept source.

FIG. 6b shows a schematic of an exemplary free-space based MEMS tunable quantum dot VCSEL swept source of the present invention (100b) that produces optical output 209b. This embodiment comprises a MEMS tunable quantum dot VCSEL 201 (such as one shown in FIG. 2, or in FIGS. 3, 4a and 4b), isolator 211, SOA 212, isolator 213, and a beam splitter 214. In this embodiment, two outputs, optical output 215b and wavelength monitoring/k-clock 210b, are created by the beam splitter 214. Items 211, 212, 213, 214, 215b, and 210b are off-the-shelf items that can be used without much modification.

Tunable Wavelength Range

The combination of a QD active region and a MEMS tunable DBR, as described herein and exemplified in FIGS. 2 and 3, has not previously been reported. The tunable wavelength range of the swept source from such a combination is preferably greater than 100 nm. Typically, the tunable wavelength range of a single swept source is from 100-200 nm, i.e., may be up to 110 nm, up to 120 nm, up to 150 nm, up to 180 nm. Variations are achieved by altering, for example, the compositions of the quantum dots, or by using combinations of quantum dots of different compositions. The tunable range is typically centered on one of three or four different bands, including but not limited to center wavelengths from 250-1950 nm for example at: 850 nm; 1,050 nm (sometimes loosely referred to as "1 micron"); 1,300 nm; 1,500; and 1,700 nm. The relevant applications of different center wavelengths depend on the tissue or other material that is being analyzed by the laser light produced by the device. The present invention is able to achieve the stated tuning range, as explained hereinbelow.

The peak wavelength of the optical gain of a QD is determined by the size and shape of the QD and its composition, as well as the barriers surrounding the QD. Although the shape of a real QD is not a rectangular solid, the gain peak wavelength for a QD formed with size a×b×c along the x-, y- and z-directions respectively, can be calculated relatively straightforwardly as follows: the emission wavelength corresponding to the transition between the quantized energy levels of the conduction and valence bands with the same quantization number is given by equation (1):

$$\lambda(\mu m) = 1.24/(E_g + E_c^{mnl} + E_v^{m'n'l'})(eV) \quad (1)$$

where $E_c^{mnl}$ and $E_v^{m'n'l'}$ are quantized energy levels in the conduction and valence band of the QD, respectively. The gain peak wavelength is a little shorter than the emission wavelength given by equation (1) due to the carrier related broadening effect. If an infinite barrier potential for the QD is assumed for the sake of simplicity, $E_c^{mnl}$ and $E_v^{m'n'l'}$ can be expressed analytically as:

$$E_c^{lmn} = E_{c0} + \frac{\hbar^2}{2m_e^*}\left[\left(\frac{l\pi}{a}\right)^2 + \left(\frac{m\pi}{b}\right)^2 + \left(\frac{n\pi}{c}\right)^2\right] \quad (2)$$

$$E_v^{l'm'n'} = E_{v0} - \frac{\hbar^2}{2m_h^*}\left[\left(\frac{l'\pi}{a}\right)^2 + \left(\frac{m'\pi}{b}\right)^2 + \left(\frac{n'\pi}{c}\right)^2\right] \quad (3)$$

where $E_{c0}$ is the conduction-band edge energy, $E_{v0}$ is the valence band edge energy, $m_e^*$ and $m_h^*$ are the effective mass of the electrons and the holes, respectively, $\hbar$ is "h-bar" (the Planck constant h divided by $2\pi$). Integers l, m, and n are quantum numbers that denote the labels of the quantized energy levels. The lowest energy level corresponds to l=m=n=1 (or l'=m'=n'=1). The gain peak appears around the quantized energy level. Therefore, the gain peak wavelength is determined by the dot size, and the dimensions a, b and c. In this way, the gain peak wavelength can be changed by changing the size of a QD. A QD with larger size has a second quantized state (either of l, m, or n (or l', m', n') is larger than 1) with higher energy that has a gain peak at shorter wavelength side. These two gain peaks make a broad gain spectrum.

The detail of the gain spectrum of QD's is described in (S. L. Chuang, *Physics of Photonic Devices*, John Wiley & Sons 2009, pp. 376-381, incorporated herein by reference). As noted in equations (1) and (2), the energy levels are also determined by the effective masses $m_e^*$ and $m_h^*$ of the carriers, and the band edge energies $E_{c0}$ and $E_{v0}$, which are related to the compositions of the QD's and the respective barriers. The size and shape of QD's in each QD layer can be adjusted by varying crystal growth condition and composition selection: therefore, the gain peak wavelength can have a distribution which will produce a broader gain spectrum. A gain bandwidth of 65 nm has been reported in the publication Takada, et al., "10.3 Gb/s operation over a wide temperature range in 1.3 μm quantum-dot DFB lasers with high modal gain", Optical Fiber Communication Conference\National Fiber Optic Engineers Conference, Technical Digest (2010), incorporated herein by reference.

In other work, the gain bandwidth of QD's can further be broadened by combining QD's and a quantum well (QW): the quantized energy level of the QW is chosen to be higher than the second quantized energy level of the QD, providing another gain peak to broaden the gain bandwidth. Using this method, a total gain bandwidth of more than 200 nm has been achieved. In this work, a gain bandwidth of 160 nm from QD's alone was shown. The detail is described in (S. Chen, K. Zhou, Z. Zhang, J. R. Orchard, D. T. D. Childs, M. Hugues, O. Wada, and R. A. Hogg, "Hybrid quantum well/quantum dot structure for broad spectral bandwidth emitters", *IEEE J. Selected Topics of Quantum Electron.*, vol. 19, No. 4, July/August 2013, incorporated herein by reference). But the structures described in the two references cited in this and the preceding paragraph are not sufficient to achieve the lasing wavelength tuning of a widely tunable laser or a swept source.

As explained hereinabove, the present invention provides a MEMS tunable quantum dot VCSEL (with an exemplary embodiment emitting a center wavelength around 1,300 nm). This present invention at solves at least two problems in the prior art. First, the problem of insufficient DBR reflectivity bandwidth of InP based DBR's in the prior art is solved by using a GaAs based DBR with broader reflectivity bandwidth. Second, the problem of a complicated wafer bonding process that was believe to be necessary in the prior art to bond an InP based active region wafer to a GaAs based DBR wafer, is obviated by using a quantum dot active region continuously grown on top of a GaAs based DBR, which is grown on a GaAs substrate.

All references cited herein are incorporated by reference in their entireties.

The foregoing description is intended to illustrate various aspects of the instant technology. It is not intended that the examples presented herein limit the scope of the appended claims. The invention now being fully described, it will be apparent to one of ordinary skill in the art that many changes and modifications can be made thereto without departing from the spirit or scope of the appended claims.

What is claimed:

1. A microelectromechanical system (MEMS) tunable vertical cavity surface-emitting laser (VCSEL) comprising an air gap, an anti-reflective (AR) coating, and one or more layers of quantum dots situated in between an upper and a lower distributed Bragg reflector (DBR), wherein the VCSEL has a tunable range of 100-200 nm, and the one or more layers of quantum dots comprise quantum dots having a center wavelength in the range of 250-1950 nm.

2. The MEMS tunable VCSEL of claim 1, wherein the one or more layers of quantum dots comprise InAs or InGaAs quantum dots, and are separated by InGaAs barrier layers.

3. The MEMS tunable VCSEL of claim 1, wherein each of the DBRs comprises multiple pairs of alternating layers of material.

4. The MEMS tunable VCSEL of claim 3, wherein the alternating layers of material comprise GaAs or AlGaAs.

5. The MEMS tunable VCSEL of claim 1, wherein the one or more layers of quantum dots are in an active region grown continuously on the lower DBR.

6. The MEMS tunable VCSEL of claim 1, wherein the one or more layers of quantum dots comprise quantum dots having a center wavelength in the range of 850-1700 nm.

7. The MEMS tunable VCSEL of claim 1, wherein the one or more layers of quantum dots comprise more than one size or more than one composition of quantum dot.

8. An optical coherence tomography system comprising the tunable VCSEL of claim 1.

9. An electrostatically actuated MEMS tunable VCSEL of claim 1.

* * * * *